(12) United States Patent
Guglieri et al.

(10) Patent No.: US 8,969,621 B2
(45) Date of Patent: Mar. 3, 2015

(54) ETHER-AMIDE COMPOUNDS AND PREPARATION AND USES THEREOF

(75) Inventors: Massimo Guglieri, Monaco (MC); Olivier Jentzer, Vourles (FR)

(73) Assignee: Rhodia Operations, Aubervilliers (FR)

( * ) Notice: Subject to any disclaimer, the term of this patent is extended or adjusted under 35 U.S.C. 154(b) by 541 days.

(21) Appl. No.: 12/990,293

(22) PCT Filed: Apr. 30, 2009

(86) PCT No.: PCT/EP2009/055287
§ 371 (c)(1),
(2), (4) Date: Mar. 16, 2011

(87) PCT Pub. No.: WO2009/133181
PCT Pub. Date: Nov. 5, 2009

(65) Prior Publication Data
US 2011/0263898 A1   Oct. 27, 2011

(30) Foreign Application Priority Data

Apr. 30, 2008 (FR) ...................... 08 02433

(51) Int. Cl.
*C07C 233/05* (2006.01)
(52) U.S. Cl.
USPC .......................... 564/201; 564/131
(58) Field of Classification Search
USPC ................................ 564/201, 131
See application file for complete search history.

(56) References Cited

U.S. PATENT DOCUMENTS

| 2,704,280 | A |   | 3/1955 | Rutherford |
| 2,719,176 | A | * | 9/1955 | Coover, Jr. et al. ........... 564/130 |
| 3,904,635 | A | * | 9/1975 | Senoo et al. .................. 546/245 |

FOREIGN PATENT DOCUMENTS

| GB | 870029 A | * | 6/1961 |
| JP | 02045456 | * | 2/1990 |
| JP | 02083358 | * | 3/1990 |
| JP | 402083358 | * | 3/1990 |
| JP | 402088567 | * | 3/1990 |
| JP | 02124858 | * | 5/1990 |
| JP | 408002850 B2 | * | 1/1996 |
| JP | 2005 047885 A |   | 2/2005 |
| JP | 2008 031112 A |   | 2/2008 |
| WO | WO 2006/075373 | * | 7/2006 |

OTHER PUBLICATIONS

Downey et al, Journal of Organic Chemistry, 73(8), 3299-3302, 2008.*
Hoskins et al, J. of the Chemical Society, Perkin Transactions I, 1972-1999, 1977, (5), 538-544.*
International Search Report for corresponding PCT/EP2009/055287 issued Sep. 23, 2009, in English.

\* cited by examiner

*Primary Examiner* — Shailendra Kumar
(74) *Attorney, Agent, or Firm* — Dentons US LLP

(57) ABSTRACT

Novel ether-amide compounds having the formula $R^aR^bC(OR^1)$—$CHR^c$—$CONR^2R^3$ and processes for the preparation and use thereof, especially as solvents, for example in phytosanitary formulations.

27 Claims, No Drawings

ETHER-AMIDE COMPOUNDS AND PREPARATION AND USES THEREOF

CROSS-REFERENCE TO EARLIER APPLICATIONS

This application is the U.S. national stage of International Application No. PCT/EP2009/055287, filed Apr. 30, 2009, and designating the United States (published in the French language on Nov. 5, 2009 as WO/2009/133181; the title and abstract were also published in English), which claims priority under 35 U.S.C. §119 of FR 08 02433, filed Apr. 30, 2008, each hereby expressly incorporated by reference in its entirety and each assigned to the assignee hereof.

A subject matter of the present invention is novel compounds of ether-amide type. Another subject matter of the present invention is a process for the preparation of such compounds. Another subject matter of the present invention is uses of such compounds, in particular as solvents, for example in plant-protection formulations.

Industry uses numerous chemical compounds as solvents, for example for preparing chemicals and materials, for formulating chemical compounds or for treating surfaces. For example, solvents are used for the formulation of plant-protection active principles, in particular in the form of emulsifiable concentrates (EC) intended to be diluted in water by the farmer, before application over a field.

Industry is on the lookout for novel compounds which make it possible to vary or to optimize products and processes in which solvents, in particular polar solvents, are to be used. Industry needs in particular compounds of modest cost exhibiting advantageous operational properties. Industry also needs compounds exhibiting a toxicological and/or ecological profile perceived as favorable, in particular a low volatility (low content of VOCs), a good biodegradability, a low toxicity and/or a low level of danger.

The use of dialkylamides as solvents is known. These are a product of formula R—CONMe$_2$ where R is a hydrocarbon group, such as an alkyl, typically with 6 to 30 carbon atoms. Such products are sold in particular under the name Genagen® by Clariant. These solvents have applications in particular in the plant-protection field. However, these solvents exhibit a restricted operating range and do not make it possible to dissolve certain plant-protection active principles at certain concentrations, within serviceable temperature ranges, without formation of crystals.

A need remains for novel solvents, in particular in plant-protection formulations, and for novel compounds, which can in particular broaden the range of active principles which can be formulated and/or their concentration and/or which can broaden the operating conditions, in particular in terms of stability, for example without formation of crystals, at low temperature.

The present invention meets at least one of the needs expressed above by providing a compound of following formula (I):

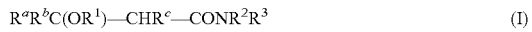

$$R^aR^bC(OR^1)\text{—}CHR^c\text{—}CONR^2R^3 \quad (I)$$

where

R$^a$, R$^b$ and R$^c$, which are identical or different, are groups chosen from the hydrogen atom and linear or branched alkyl groups, preferably C$_1$-C$_3$ alkyl groups, R$^1$ is an R$^{\prime 1}$ or -(AO)$_n$R$^{\prime 1}$ group, where R$^{\prime 1}$ is a group chosen from hydrocarbon groups comprising an average number of carbon atoms ranging from 1 to 36 which are saturated or unsaturated, linear or branched, optionally cyclic and optionally aromatic, it being possible for said aromatic groups to comprise a heteroatom in an aromatic ring, AO, which are identical or different, represent a group of formula —CH$_2$—CH$_2$—O—, —CHMe-CH$_2$—O— or —CH$_2$—CHMe-O—, n is an average number greater than or equal to 0, for example ranging from 0 to 50, R$^2$ and R$^3$, which are identical or different, are groups chosen from the hydrogen atom and hydrocarbon groups comprising an average number of carbon atoms ranging from 1 to 36 which are saturated or unsaturated, linear or branched, optionally cyclic, optionally aromatic and optionally substituted, it being possible for R$^2$ and R$^3$ together to optionally form a ring which is optionally substituted and/or which optionally comprises a heteroatom, R$^2$ and R$^3$ are not simultaneously hydrogen atoms.

Another subject matter of the invention is a process for the preparation of the compound. Another subject matter of the invention is the use of the compound as surfactant, solvent, cosolvent, stripping agent, crystallization inhibitor, cleaning agent, degreasing agent, plasticizing agent or coalescence agent. Another subject matter of the invention is a method of solvating, cosolvating, plasticizing, coalescing and/or inhibiting crystallization by addition of the compound of the invention. Another subject matter of the invention is formulations comprising the compound of the invention. The formulations can in particular be plant-protection formulations.

DEFINITIONS OR ABBREVIATIONS

In the present patent application, use is made in particular of the following abbreviations: Me means methyl, Et means ethyl, IsoAm means isoamyl and cyclo means cyclohexyl.

In the present patent application, the term "material composition" is understood to mean a more or less complex composition comprising several chemical compounds. It can typically be an unpurified or incompletely purified reaction product. The compound of the invention can in particular be isolated and/or sold and/or used in the form of a material composition comprising it. The compound of the invention, in the form of a pure molecule or in the form of a mixture corresponding to the formula (I), can be included in the material composition.

In the present patent application, the term "solvent" is understood within a broad sense, covering in particular the functions of cosolvent, of crystallization inhibitor or of stripping agent. The term "solvent" can particularly denote a product which is liquid at the operating temperature, preferably with a melting point of less than or equal to 20° C., preferably 5° C., preferably 0° C., which can contribute to rendering a solid material liquid or to preventing or slowing down the solidification or the crystallization of material in a liquid medium.

Compound of the Invention

The compound of the invention exhibits the general formula (I) given above. It should be noted that a mixture of several compounds of general formula (I) may be involved. In other words, the compound can be alone or as a mixture. In the context of mixtures of several compounds, the numbers of atoms or of units can be expressed as average numbers. These are number-average numbers. In the case of compounds alone, they will generally be whole numbers, as regards the number of carbon atoms.

The R$^a$, R$^b$ and R$^c$ groups, which are identical or different, are groups chosen from the hydrogen atom and linear or branched alkyl groups. The alkyls can in particular be C$_1$-C$_6$, preferably $C_1$-$C_3$, alkyls. They can in particular be methyl or ethyl groups. According to a specific embodiment, the total number of carbon atoms, excluding the $R^1$, $R^2$ and $R^3$ groups, is 4, 5 or 6.

It is mentioned that, according to a specific embodiment, at least one of the groups chosen from $R^a$, $R^b$ and $R^c$ is other than the hydrogen atom, for example a group chosen from linear or branched alkyl groups. The alkyls can in particular be $C_1$-$C_6$, preferably $C_1$-$C_3$, alkyls. They can in particular be methyl or ethyl groups. According to a specific embodiment, the total number of carbon atoms, excluding the $R^1$, $R^2$ and $R^3$ groups, is 4, 5 or 6.

According to a specific embodiment, $R^c$ is a methyl group and $R^a$ and $R^b$, which are identical or different, can be groups chosen from the hydrogen atom and linear or branched alkyl groups. The alkyls can in particular be $C_1$-$C_6$, preferably $C_1$-$C_3$, alkyls. They can in particular be methyl or ethyl groups. According to a specific embodiment, the total number of carbon atoms, excluding the $R^1$, $R^2$ and $R^3$ groups, is 4, 5 or 6.

According to a specific embodiment, $R^c$ is a hydrogen atom and $R^a$ is a group chosen from the hydrogen atom and linear or branched alkyl groups, and $R^b$ is a group chosen from linear or branched alkyl groups. The alkyls can in particular be $C_1$-$C_6$, preferably $C_1$-$C_3$, alkyls. They can in particular be methyl or ethyl groups. According to a specific embodiment, the total number of carbon atoms, excluding the $R^1$, $R^2$ and $R^3$ groups, is 4, 5 or 6.

It is mentioned that $R^a$ can be a group chosen from linear or branched alkyl groups. The alkyls can in particular be $C_1$-$C_6$, preferably $C_1$-$C_3$, alkyls. They can in particular be methyl or ethyl groups. According to a specific embodiment, the total number of carbon atoms, excluding the $R^1$, $R^2$ and $R^3$ groups, is 4, 5 or 6.

It is mentioned that $R^b$ and $R^c$, which are identical or different, can be groups chosen from the hydrogen atom and linear or branched alkyl groups. The alkyls can in particular be $C_1$-$C_6$, preferably $C_1$-$C_3$, alkyls. They can in particular be methyl or ethyl groups. According to a specific embodiment, the total number of carbon atoms, excluding the $R^1$, $R^2$ and $R^3$ groups, is 4, 5 or 6.

According to a specific embodiment:

$R^a$ is a group chosen from linear or branched alkyl groups. The alkyls can in particular be $C_1$-$C_6$, preferably $C_1$-$C_3$, alkyls. They can in particular be methyl or ethyl groups. According to a specific embodiment, the total number of carbon atoms, excluding the $R^1$, $R^2$ and $R^3$ groups, is 4, 5 or 6.

$R^b$ and $R^c$, which are identical or different, are groups chosen from the hydrogen atom and linear or branched alkyl groups. The alkyls can in particular be $C_1$-$C_6$, preferably $C_1$-$C_3$, alkyls. They can in particular be methyl or ethyl groups. According to a specific embodiment, the total number of carbon atoms, excluding the $R^1$, $R^2$ and $R^3$ groups, is 4, 5 or 6.

According to specific embodiments, $R^c$=H and $R^b$=H or $R^c$=Me and $R^b$=H or $R^c$=H and $R^b$=Me. According to specific embodiments, $R^a$ is a methyl or ethyl group.

According to a specific embodiment, $R^c$=H and $R^b$=H and $R^a$=Et. This specific embodiment can, for example, be implemented by conversion starting from an alkenenitrile of formula (I') of 2-pentenenitrile (sometimes denoted 2PN) type. It can in particular be cis-2-pentenenitrile or trans-2-pentenenitrile.

According to another specific embodiment, $R^c$=Me and $R^b$=H and $R^a$=Me or $R^c$=H and $R^b$=Me and $R^a$=Me. This specific embodiment can, for example, be implemented by conversion starting from an alkenenitrile of formula (I') of methyl-2-butenenitrile (sometimes denoted 2BN) type. It can in particular be a 2-methyl-2-butenenitrile, such as cis-2-methyl-2-butenenitrile or trans-2-methyl-2-butenenitrile, or a 3-methyl-3-butenenitrile, such as cis-3-methyl-2-buteneni-trile or trans-3-methyl-2-butenenitrile.

According to a specific embodiment, the compound is a mixture of compounds such as $R^c$=H and $R^b$=H and $R^a$=Et for the first and $R^c$=Me and $R^b$=H and $R^a$=Me for the second. The molar ratio of the first and second can, for example, be between 50/50 and 99/1, preferably between 60/40 and 90/10.

The $R^2$ and $R^3$ groups, which are identical or different, are groups chosen from the hydrogen atom and hydrocarbon groups comprising an average number of carbon atoms ranging from 1 to 36 which are saturated or unsaturated, linear or branched, optionally cyclic, optionally aromatic and optionally substituted, it being possible for $R^2$ and $R^3$ together to optionally form a ring which comprises the nitrogen atom to which they are bonded, which is optionally substituted and/or which optionally comprises an additional heteroatom. It should be noted that $R^2$ and $R^3$ are not simultaneously hydrogen atoms. In other words, the —$CONR^2R^3$ group is not a —$CONH_2$ group. It can be a —$CONHR^2$ group, where $R^2$ is not a hydrogen atom, or a —$CONR^2R^3$ group, where $R^2$ and $R^3$ are not hydrogen atoms. $R^2$ and $R^3$, which are identical or different, can, for example, be chosen from methyl, ethyl, propyl (n-propyl), isopropyl, n-butyl, isobutyl, n-pentyl, amyl, isoamyl, hexyl or cyclohexyl groups, their mixtures and/or their combinations. $R^2$ and $R^3$ can also be such that they together form, with the nitrogen atom, a morpholine, piperazine or piperidine group. $R^2$ and $R^3$ can in particular be methyl groups, preferably both.

The $R^1$ group is a group typically corresponding to an alcohol $R^1$—OH. In one case, it can correspond to a simple alcohol $R'^1$—OH. In another case, it can correspond to an ethoxylated and/or propoxylated alcohol of formula HO-$(AO)_nR'^1$. $R'^1$ represents the hydrocarbon residue of its optionally ethoxylated and/or propoxylated alcohols. The $R'^1$ group is a group chosen from hydrocarbon groups comprising an average number of carbon atoms ranging from 1 to 36 which are saturated or unsaturated, linear or branched, optionally cyclic and optionally aromatic, it being possible for said aromatic groups to comprise a heteroatom in an aromatic ring. The heteroatom of the aromatic group can be an oxygen or nitrogen atom. It is mentioned that the aromatic group can be directly connected or can be carried by an alkyl group. It is mentioned that the cyclic or aromatic groups can be substituted. $R'^1$ can, for example, be chosen from methyl, ethyl, propyl, isopropyl, n-butyl, isobutyl, n-pentyl, isopentyl, isoamyl, n-hexyl, cyclohexyl, n-octyl, isooctyl, 2-ethylhexyl, tridecyl, phenyl or benzyl groups and their mixtures. It should be noted that $R'^1$ can be a more or less complex mixture which can correspond to the use of a more or less complex mixture of $R^1$—OH alcohols, for example fusel oil.

According to a specific embodiment, $R^1$ is a group other than n-hexyl and $R^a$ and/or $R^b$ is other than the hydrogen atom. According to a specific embodiment, $R^1$ is a group other than n-butyl and $R^a$ and/or $R^b$ is other than the hydrogen atom. According to a specific embodiment, $R^1$ is a group other than ethylhexyl and $R^a$ and/or $R^b$ is other than the hydrogen atom.

According to a specific embodiment, $R^1$ is a group other than n-hexyl. According to a specific embodiment, $R^1$ is a group other than n-butyl. According to a specific embodiment, $R^1$ is a group other than ethylhexyl.

According to a specific embodiment, the R¹ group is a cyclic group, preferably a cyclohexyl group. According to a specific embodiment, $R^a=R^b=R^c=H$ and $R^1$ is a cyclic group, preferably a cyclohexyl group. The compounds exhibiting such a group exhibit solvent properties and/or properties of miscibility in water which are particularly advantageous, in particular in the context of plant-protection formulations.

The group (AO) represents an ethoxy group of formula —CH₂—CH₂—O— or a propoxy group of formula —CHMe-CH₂—O— or —CH₂—CHMe-O—. The number n is an average number greater than or equal to 0, for example ranging from 0 to 50. It typically represents a degree of ethoxylation and/or propoxylation. In the case where ethoxy and propoxy groups are present, they can be distributed randomly or blockwise.

The compound of the invention is preferably such that it exhibits a melting point of less than or equal to 20° C., preferably 5° C., preferably 0° C. The groups described in detail above are preferably such that the compound exhibits this property.

According to one embodiment, the compound of the invention can be completely miscible in water. According to a specific embodiment, the compound of the invention is partially miscible in water. The miscibility in water can, for example, be less than 10% by weight (at 25° C.), preferably than 2%, preferably than 1% or than 0.1%. It can be greater than 0.001%, preferably than 0.01% or than 0.1%. It can, for example, be between 0.01% and 2%, for example between 0.1% and 1%. Surprisingly, the compounds of the invention exhibit good solvent properties, in particular for plant-protection active principles in plant-protection formulations with a low miscibility in water. The $R^a$, $R^b$ and $R^c$ groups and/or the $R^1$ group and/or the $R^2$ and $R^3$ groups can be chosen so as to control the miscibility in water.

The compound of the invention preferably exhibits one of the following formulae:

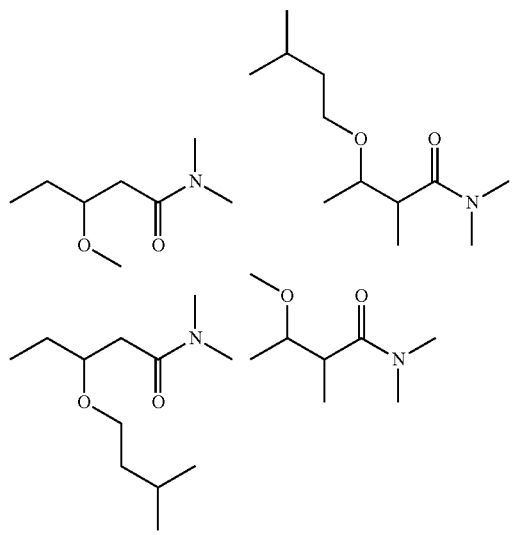

It is mentioned that the compound can be a mixture of compounds exhibiting these formulae. For example, the following mixtures may be involved:

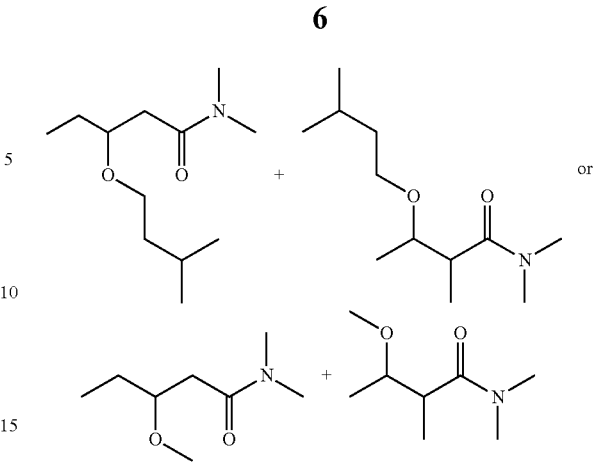

It is mentioned that the compound of the invention can be included in a material composition comprising products other than the compound alone or as a mixture corresponding to the formula (I). In the material composition, the compound of the invention can represent at least 10% by weight. Preferably, it is the main compound of the material composition. The term "main compound" is understood to mean, in the present patent application, the compound having the highest content, even if its content is less than 50% by weight (for example, in a mixture of 40% of A, of 30% of B and of 30% of C, the product A is the main compound). More preferably still, the compound of the invention represents at least 50% by weight of the material composition, for example from 70 to 95% by weight and even from 75 to 90% by weight. As indicated above, the material composition can be a reaction product. The other products of the material composition can in particular be by-products of the impurities, unreacted products or products corresponding to reaction adducts of products included in the starting compounds not leading to the compounds of formula (I).

Process

The compound of the invention can in particular be prepared by conversion starting from an alkenenitrile of formula (I')

$$R^aR^bC=CR^c-CN \qquad (I').$$

It should be noted that, in all the processes and sequences mentioned below, use may be made of optional intermediate stages of separation and/or of purification in order, for example, to remove untargeted by-products. The by-products can optionally be used to manufacture other products or can be converted in order to be reintroduced into the process. The process can be followed by stages of filtration and/or of purification, for example by distillation.

It is possible in particular to carry out a conversion by a process comprising a conversion by addition of an alcohol of formula R¹—OH to the double bond and a conversion of the —CN group to the —CONR²R³ group. These conversions can be carried out in any order. However, it is preferable to carry out the addition of the alcohol before the conversion of the —CN group.

The addition of the alcohol can be carried out in a known way, for example in the presence of a base, often in a catalytic amount. It is an addition of the Michael type. It can be carried out in a solvent, preferably in a nonaqueous solvent. Use may advantageously be made, as solvent, of the alcohol of formula R¹—OH, then in excess.

The conversion of the —CN group can in particular comprise a conversion of the —CN group to the —COOH or —COOR' group, where R' is a $C_1$-$C_4$ alkyl, followed by a conversion of the —COOH or —COOR' group to the —CONR$^2$R$^3$ group using an amine of formula HNR$^2$R$^3$.

In one embodiment, the process comprises the following stages:
stage 1) the alkenenitrile of formula (I') is reacted with an alcohol of formula R$^1$—OH in order to obtain an ether-nitrile of formula (II')

$$R^aR^bC(OR^1)\text{—}CHR^c\text{—}CN \qquad (II')$$

stage 2) the —CN group of the ether-nitrile is converted to the amide group, so as to obtain the product of formula (I).

Stage 1) typically constitutes a Michael reaction. As mentioned above, it can be carried out in the presence of a base, preferably in a nonaqueous solvent, for example the alcohol of formula R$^1$—OH, typically in large excess. Use may be made, as base, for example, of an ammonium hydroxide, an alkali metal, and the like.

Stage 2) typically constitutes a conversion of the —CN group to the —CONR$^2$R$^3$ group. Stage 2) advantageously comprises the following stages:
stage 2a): the —CN group is converted to the —COOH or —COOR' group, where R' is a $C_1$-$C_4$ alkyl,
stage 2b): the —COOH or —COOR' group is converted to the —CONR$^2$R$^3$ group using an amine of formula HNR$^2$R$^3$, so as to obtain the compound of formula (I).

According to a specific embodiment, stage 2) comprises the following stages:
2a') the —CN group is converted to the —COOH group directly by hydrolysis or by forming a —COOR' group and by then hydrolyzing,
2b') the —COOH group is converted to the —CONR$^2$R$^3$ group directly by reaction with an amine of formula HNR$^2$R$^3$ or by forming a —COCl group and by then reacting with an amine of formula HNR$^2$R$^3$, so as to obtain the compound of formula (I).

Use may in particular be made of the following sequence:
2a'1) the —CN group is converted to the —COOH group by hydrolysis,
2b'1) the —COOH group is converted to the —CONR$^2$R$^3$ group directly by reaction with an amine of formula HNR$^2$R$^3$.

Use may alternatively be made of the following sequence:
2a'1) the —CN group is converted to the —COOH group by hydrolysis,
2b'2) a —COCl group is formed,
2b'3) reaction is carried out with an amine of formula HNR$^2$R$^3$.

Use may alternatively be made of the following sequence:
2a'2) a —COOR' group is formed,
2a'3) hydrolysis is carried out to give the —COOH group,
2b'1) the —COOH group is converted to the —CONR$^2$R$^3$ group directly by reaction with an amine of formula HNR$^2$R$^3$.

Use may alternatively be made of the following sequence:
2a'2) a —COOR' group is formed,
2a'3) hydrolysis is carried out to give the —COOH group,
2b'2) a —COCl group is formed,
2b'3) reaction is carried out with an amine of formula HNR$^2$R$^3$.

According to another specific embodiment, stage 2) comprises the following stages:
2a") the —CN group is converted to the —COOR' group,
2b") the —COOR' group is converted to the —CONR$^2$R$^3$ group using an amine of formula HNR$^2$R$^3$, so as to obtain the compound of formula (I).

Stage 2b") is a transamidation reaction. It can be carried out in a known way. During this reaction, it is preferable to employ from 0.8 to 1.2 mol, preferably from 0.9 to 1.1 mol, preferably approximately 1 mol, of amine per mole of ester. The reaction can in particular be carried out using acid or basic catalysts, for example using potassium carbonate or alkyl orthotitanates. This stage can be carried out in solution, for example in aqueous solution or in solution in toluene. It is possible, during this stage, to gradually remove the methanol formed in order to promote the reaction. The removal can be accompanied by a removal of the solvent, for example with an azeotrope. After separation of the methanol, the solvent removed can be reintroduced into the process.

Stages 2a") and 2a'2) are esterification reactions starting from a nitrile. They can be carried out in a known way. Use may in particular be made of the Pinner reaction. They can be carried out using an alcohol of formula R'OH, preferably in excess. This alcohol can constitute the solvent of the reaction.

Stage 2a'1) is a hydrolysis reaction. It can be carried out in a known way, in particular by acid hydrolysis or basic hydrolysis.

Stage 2b'2) is a known reaction. It can in particular be carried out using thionyl chloride. It is accompanied by the formation of hydrochloric acid. A base can be used in order to trap it, for example triethylamine (TEA). This stage can be carried out with at least 0.8 molar equivalent of amine, preferably with at least one equivalent. Use may in particular be made of an excess of 1.05 to 1.4 molar equivalents.

The addition of the alcohol, in particular in stage 1), is preferably carried out using at least one molar equivalent of alcohol, with respect to the alkenenitrile. Use may be made of a large excess of alcohol, for example from 2 to 20 equivalents, in particular from 5 to 15. Use may in particular be made of the alcohol as solvent of the reaction.

Use may in particular be made, as starting alkenenitrile compounds, of the alkenenitriles for which:
$R^c$=H and $R^b$=H and $R^a$=Et. It is an alkenenitrile of formula (I') of 2-pentenenitrile (sometimes denoted 2PN) type. It can in particular be cis-2-pentenenitrile or trans-2-pentenenitrile.
$R^c$=Me and $R^b$=H and $R^a$=Me or $R^c$=H and $R^b$=Me and $R^a$=Me. It is an alkenenitrile of formula (I') of methyl-2-butenenitrile (sometimes denoted 2BN) type. It can in particular be a 2-methyl-2-butenenitrile, such as cis-2-methyl-2-butenenitrile or trans-2-methyl-2-butenenitrile, or a 3-methyl-2-butenenitrile, such as cis-3-methyl-2-butenenitrile or trans-3-methyl-2-butenenitrile.

Use may in particular be made of a mixture of alkenenitriles, where $R^c$=H and $R^b$=H and $R^a$=Et for the first and $R^c$=Me and $R^b$=H and $R^a$=Me for the second. The molar ratio of the first to the second can, for example, be between 50/50 and 99/1, preferably between 60/40 and 90/10. Use may in particular be made of a mixture of cis-2-pentenenitrile (the first) and of trans-2-methyl-2-butenenitrile (the second), for example in a molar ratio of the first to the second of between 50/50 and 99/1, preferably between 60/40 and 90/10.

The compound of the invention can alternatively be prepared by conversion starting from an unsaturated compound of following formula $R^aR^bC$=$CR^c$—CO—NR$^1$R$^2$, for example starting from acrylamide compounds (where $R^c$=H) or from methacrylamide compounds (where $R^c$=CH$_3$). It is possible, for example, to operate by Michael addition, by reaction of an alcohol or of an alkoxide of formula R$^1$—OH or R$^1$O$^-$ with a double bond. Such reactions are known to a person skilled in the art. They can be carried out in the presence of a basic catalyst.

The compound of the invention can alternatively be prepared by conversion starting from an unsaturated compound of following formula $R^aR^bC$=$CR^c$—COOH or $R^aR^bC$=$CR^c$—COOR' or $R^aR^bC$=$CR^c$—CONH$_2$. It is possible, for example, to carry out a Michael addition and then to convert the —COOH or —COOR' or —CONH$_2$ group to the —CONR$^2$R$^3$ group by amidation or transamidation or a substitution reaction. It is alternatively possible to convert the —COOH or —COOR' or —CONH$_2$ group to the —CONR$^2$R$^3$ group by amidation or transamidation or a substitution reaction and then to carry out a Michael addition.

Uses—Formulations

The compound of the invention can in particular be used as surfactant, solvent, cosolvent and/or crystallization inhibitor, as plasticizing agent or as coalescence agent.

The term "cosolvent" is understood to mean that other solvents can be combined with it. The use as solvent or cosolvent comprises in particular uses for dissolving a compound in a formulation, in a reaction medium, the use for completely or partially dissolving a product to be removed (degreasing, stripping) and/or the use for facilitating the detachment of films of materials.

For the use as surfactant, preference is given to the alkoxylated and/or propoxylated compounds, that is to say where n is other than 0 in the formula (I).

The compound of the invention can be used in particular, for the functions indicated above or for others, in a plant-protection formulation, in a cleaning formulation, in a stripping formulation, in a degreasing formulation, in a lubricants or textiles formulation, in a coating formulation, for example in a paint formulation, in a pigment or ink formulation or in a plastic formulation.

The compound can, for example, be used as coalescence agent in a water-based paint formulation.

The compound can in particular be used as solvent for resins, for example in the industry for coating cables or in the electronics industry, in particular as solvent for PVDF.

The compound can be used in particular as cleaning and/or stripping solvent in the electronics industry. It can in particular be used in lithium batteries. It can be used in particular on photoresist resins, polymers, waxes, greases or oils.

The compound can be used in particular for the cleaning of inks, for example during the production of inks or during the use of ink in printing.

The compound can be used in particular for the cleaning of sieves or other implements employed in processes for the manufacture and/or recycling of paper.

The compound can be used in particular for the cleaning of asphalts or tar sands, for example on coated substrates, on the implements used to apply these materials, on contaminated clothing or on contaminated vehicles.

The compound can be used in particular for the cleaning of flying craft, such as planes, helicopters or space shuttles.

The compound can be used in particular as degreasing agent on metal surfaces, for example surfaces of implements, manufactured items, metal sheets or molds, in particular made of steel or aluminum or of alloys of these metals.

The compound can in particular be used as cleaning solvent on hard surfaces or textile surfaces.

The compound can be used in particular as solvent for stripping paints or resins on surfaces of implements, for example casting molds, or on surfaces of industrial sites (floors, partitions, and the like). The formulations for stripping paints can in particular be water-based formulations (the compound being as a mixture with water) or solvent-based formulations (the compound then being the solvent or a compound as a mixture with water).

The compound can be used in particular as plasticizing agent in thermoplastic polymer formulations.

The cleaning and/or degreasing formulations can in particular be formulations for household care, carried out in homes or in public areas (hotels, offices, factories, and the like). They can be formulations for cleaning hard surfaces, such as floors, surfaces of kitchen and bathroom furniture and fittings, or dishes. These formulations can also be used in the industrial sphere for degreasing manufactured products and/or for cleaning them. Such formulations can be used in particular to clean and/or strip products, implements, molds, clothes or other items.

The compound of the invention can in particular be used in plant-protection formulations comprising a solid active product. Further details are given below, where the word "solvent" can denote the compound of the invention or a material composition comprising it described above.

Detailed Use in the Context of Plant-Protection Formulations

The plant-protection formulation is generally a concentrated plant-protection formulation comprising an active compound.

Agriculture makes use of numerous active materials, such as fertilizers or pesticides, for example insecticides, herbicides or fungicides. The reference is to plant-protection active products (or active materials). Plant-protection active products are generally products in the pure or highly concentrated form. They have to be used on farms at low concentrations. To this end, they are generally formulated with other ingredients in order to make possible easy dilution in weight by the farmer. The reference is to plant-protection formulations. The dilution carried out by the farmer is generally carried out by mixing the plant-protection formulation with water.

Thus, plant-protection formulations have to make possible easy dilution in weight by the farmer in order to obtain a product in which the plant-protection product is correctly dispersed, for example in the solution, emulsion, suspension or suspoemulsion form. Plant-protection formulations thus make possible the transportation of a plant-protection product in a relatively concentrated form, easy packaging and/or easy handling for the final user. Different types of plant-protection formulations can be used according to the different plant-protection products. Mention is made, for example, of emulsifiable concentrates ("EC"), concentrated emulsions (Emulsion, oil in water, "EW"), microemulsions ("ME"), wettable powders ("WP") or water-dispersible granules ("WDG"). The formulations which it is possible to use depend on the physical form of the plant-protection product (for example solid or liquid) and on its physicochemical properties in the presence of other compounds, such as water or solvents.

After dilution in weight by the farmer, for example by mixing with water, the plant-protection product can occur in different physical forms: solution, dispersion of solid particles, dispersion of droplets of the product, droplets of solvent in which the product is dissolved, and the like. Plant-protection formulations generally comprise compounds which make it possible to obtain these physical forms. They can, for example, be surfactants, solvents, inorganic supports and/or dispersants. Very often, these compounds do not have an active nature but a nature of intermediate of help to the formulation. Plant-protection formulations can in particular be in the liquid form or in the solid form.

In order to prepare plant-protection formulations of solid plant-protection active products, it is known to dissolve the product in a solvent. The plant-protection formulation thus comprises a solution of the product in the solvent. The formulation can be in the solid form, for example in the form of a wettable powder (WP) where the solution impregnates an inorganic support, for example kaolin and/or silica. The formulation can alternatively be in the liquid form, for example in the form of an emulsifiable concentrate (EC) exhibiting a single clear liquid phase comprising the solvent and the product in solution, which can form an emulsion by addition of water, without stirring or with gentle stirring. It can also be in the form of a cloudy concentrated emulsion (EW), the phase of which dispersed in the water comprises the solvent and the product in solution in the solvent. It can also be in the form of a clear microemulsion (ME), the phase of which dispersed in the water comprises the solvent and the product in solution in the solvent.

Some solid plant-protection active principles are often difficult to formulate. For example, tebuconazole is a particularly effective and widely used fungicide, in particular for the cultivation of soya. For some plant-protection active principles, it is difficult to produce concentrated formulations which are easy to dilute for the farmer, which are stable and which are without substantial disadvantages (known or perceived) with regard to safety, toxicity and/or ecotoxicity. For some active principles, it is difficult to formulate at relatively high concentrations with a satisfactory stability. In particular, it is necessary to avoid the appearance of crystals, in particular at low temperature and/or during the dilution and/or during the storage at high temperature of the diluted composition. The crystals may have negative effects, in particular may block the filters of the devices used to spread the diluted composition, may block the spray devices, may reduce the overall activity of the formulation, may create needless problems of waste procedures in order to remove the crystals, and/or may cause poor distribution of the active product over the agricultural field.

The formulations comprising the solvent exhibit in particular:
dissolution of large amounts of active principles,
absence of crystallization, even under demanding conditions,
good biological activity, which can be due to good solvation, and/or
a safety, toxicology and/or ecotoxicology profile perceived as favorable.

The plant-protection formulation can in addition be a concentrated plant-protection formulation comprising:
a) a plant-protection active product,
b) the solvent,
c) optionally at least one emulsifying agent, preferably a surfactant, and
d) optionally water.

Plant-Protection Active Product a)

Plant-protection active products, in particular water-insoluble and solid products, are known to a person skilled in the art. The plant-protection active product can in particular be a herbicide, an insecticide, an acaricide, a fungicide or a rodenticide, for example a raticide.

Mention may be made, as nonlimiting examples of suitable active materials, inter alia, of ametryn, diuron, linuron, chlortoluron, isoproturon, metamitron, diazinon, aclonifen, atrazine, chlorothalonil, bromoxynil, bromoxynil heptanoate, bromoxynil octanoate, mancozeb, maneb, zineb, phenmedipham, propanil, the phenoxyphenoxy series, the heteroaryloxyphenoxy series, CMPP, MCPA, 2,4-D, simazine, the active products of the imidazolinone series, the family of the organophosphorus compounds, with in particular azinphos-ethyl, azinphos-methyl, alachlor, chlorpyrifos, diclofop-methyl, fenoxaprop-P-ethyl, methoxychlor, cypermethrin, fenoxycarb, cymoxanil, chlorothalonil, the neonicotinoid insecticides, the family of the triazole fungicides, such as azaconazole, bromuconazole, cyproconazole, difenoconazole, diniconazole, epoxiconazole, fenbuconazole, flusilazole, myclobutanil, tebuconazole, triadimefon and triadimenol, strobilurins, such as pyraclostrobin, picoxystrobin, azoxystrobin, famoxadone, kresoxim-methyl and trifloxystrobin, or sulfonylureas, such as bensulfuron-methyl, chlorimuron-ethyl, chlorsulfuron, metsulfuron-methyl, nicosulfuron, sulfometuron-methyl, triasulfuron and tribenuron-methyl.

The water-insoluble products are chosen from this list.

Use may in particular be made of the following plant-protection active products:

| Alachlor | 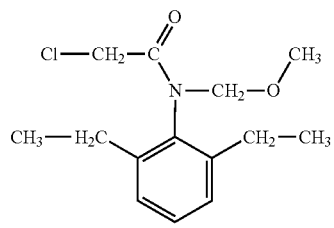 [SMILES: CCc1cccc(CC)c1N(COC)C(=O)CCl] |
|---|---|
| Chlorpyrifos | 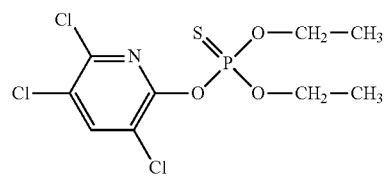 [SMILES: CCOP(=S)(OCC)Oc1nc(Cl)c(Cl)cc1Cl] |

Alpha-cypermethrin
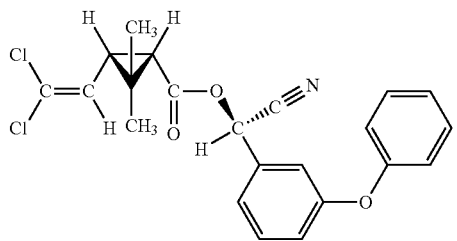
(R)-alcohol (1s)-cis-acid
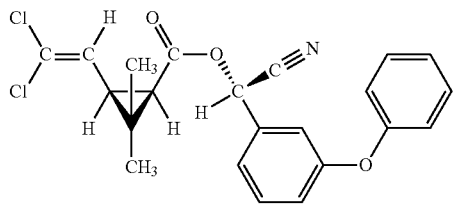
(S)-alcohol (1R)-cis-acid
As racemic mixture and/or as isolated stereoisomers.
Phenmedipham
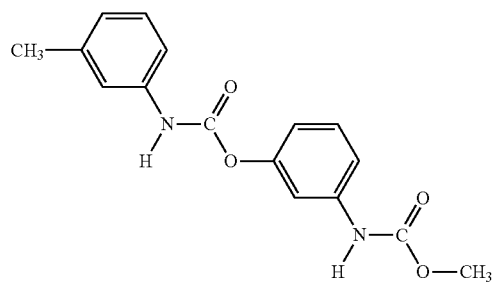
Propanil
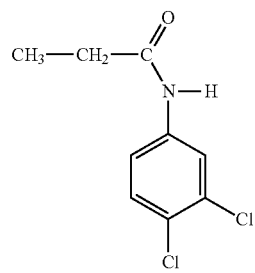
Pendimethalin
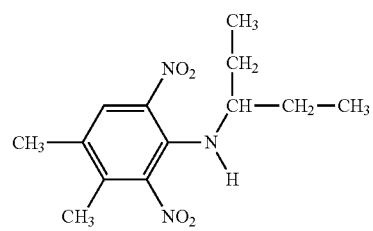 [SMILES: CCC(CC)Nc1c([N+](=O)[O-])cc(C)c(C)c1[N+](=O)[O-]]

-continued
Triadimenol
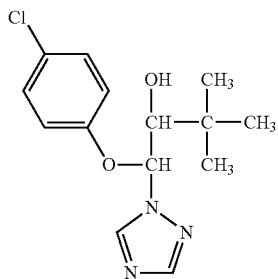 [SMILES: CC(C)(C)C(O)C(Oc1ccc(Cl)cc1)n1cncn1]
Trifluralin
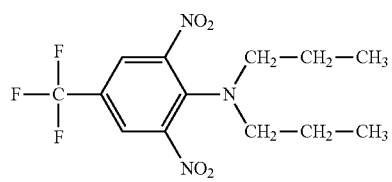 [SMILES: CCCN(CCC)c1c([N+](=O)[O-])cc(C(F)(F)F)cc1[N+](=O)[O-]]
Oxyfluorfen
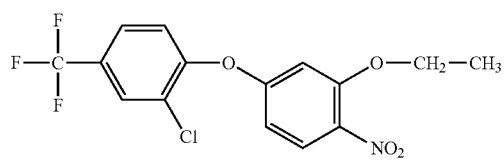 [SMILES: CCOc1cc(Oc2ccc(C(F)(F)F)cc2Cl)ccc1[N+](=O)[O-]]
Dimethoate
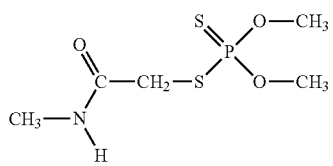
Imidacloprid
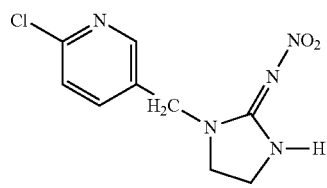 [SMILES: O=[N+]([O-])N=C1NCCN1Cc1ccc(Cl)nc1]
Propoxur
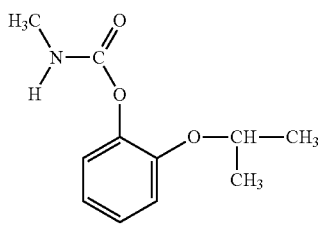
Benomyl
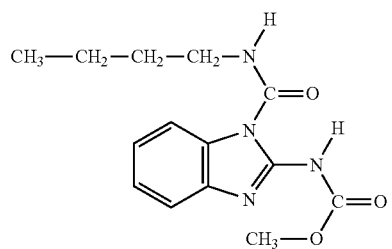 [SMILES: CCCCNC(=O)n1c(NC(=O)OC)nc2ccccc21]

-continued
Deltamethrin
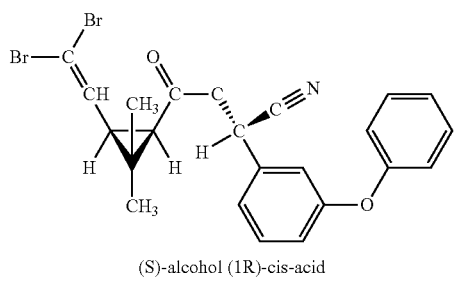 [SMILES: CC1(C)[C@H](C(=O)C[C@H](C#N)c2cccc(Oc3ccccc3)c2)[C@@H]1C=C(Br)Br]
(S)-alcohol (1R)-cis-acid
Fenvalerate
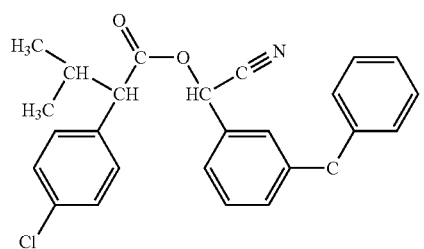 [SMILES: CC(C)C(C(=O)OC(C#N)c1cccc(Cc2ccccc2)c1)c1ccc(Cl)cc1]
Abamectin
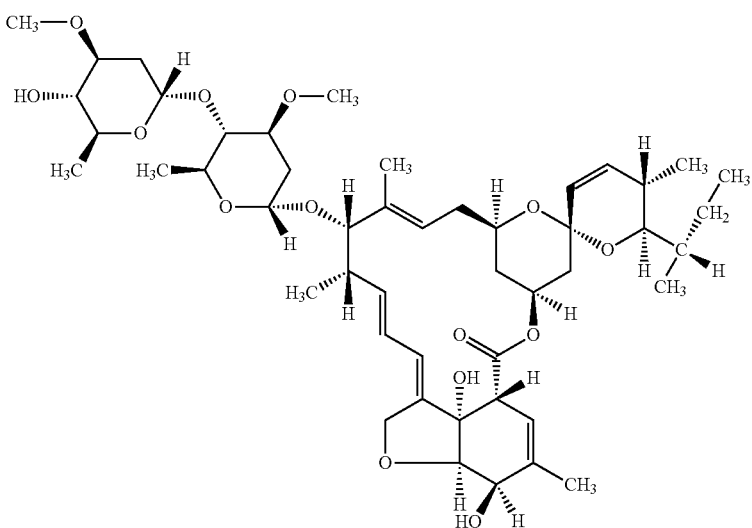
avermectin $B_{1a}$
(major component)

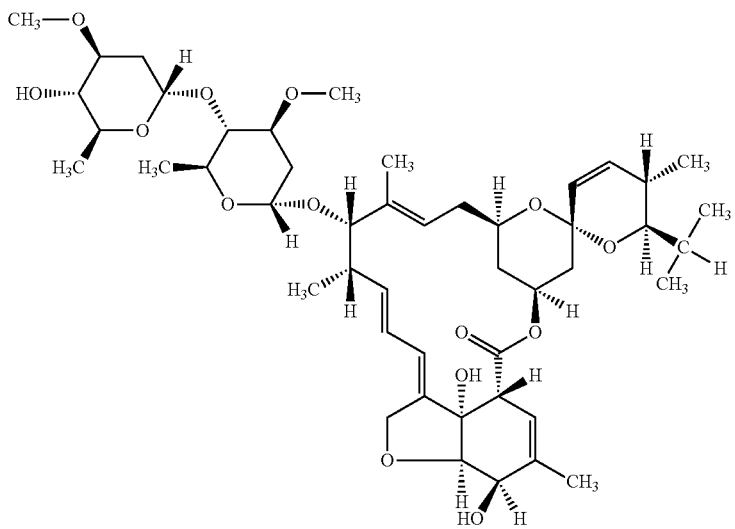
avermectin B<sub>1b</sub>
(minor component)
Amicarbazone
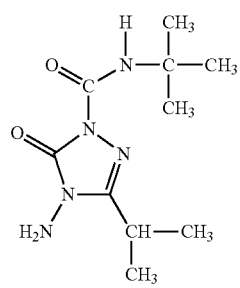 [SMILES: CC(C)c1nn(C(=O)NC(C)(C)C)c(=O)n1N]
Bifenthrin
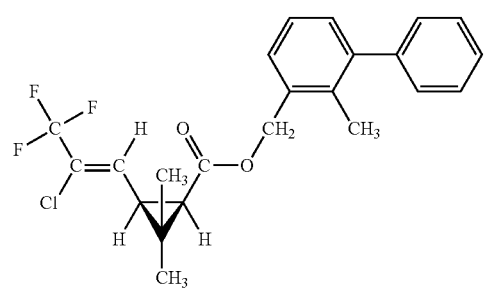
(Z)-(1R)-cis-acid
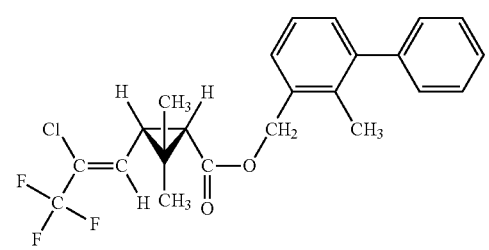
(Z)-(1S)-cis-acid -continued
Carbosulfan
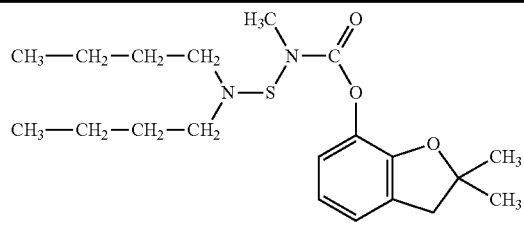
Cyfluthrin
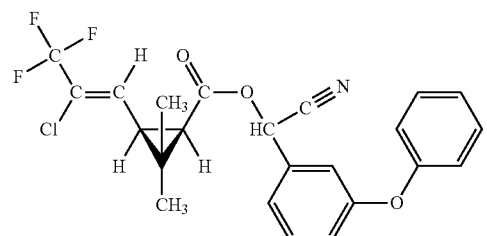
(Z)-(1R)-cis-acid
(Z)-(1s)-cis-acid
Difenoconazole
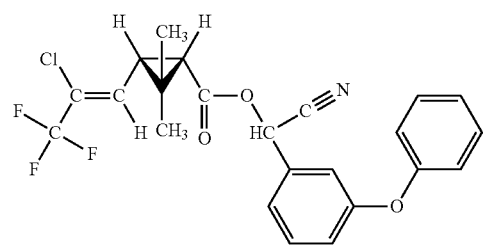
Etofenprox
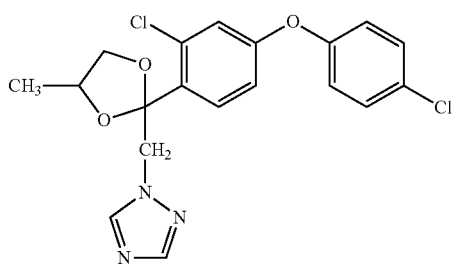 [SMILES: CC1COC(Cn2cncn2)(c2ccc(Oc3ccc(Cl)cc3)cc2Cl)O1]
Fenoxaprop-ethyl
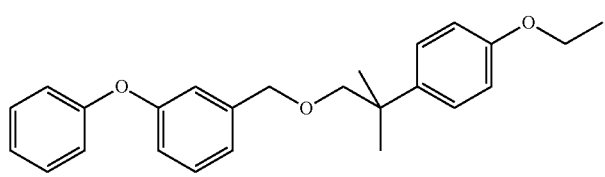 [SMILES: CCOc1ccc(C(C)(C)COCc2cccc(Oc3ccccc3)c2)cc1]

-continued
Fipronil
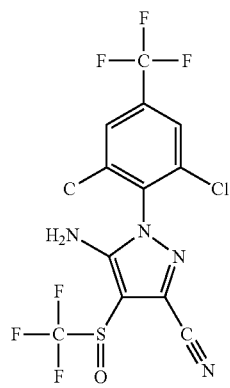 [SMILES: Cc1cc(C(F)(F)F)cc(Cl)c1-n1nc(C#N)c(S(=O)C(F)(F)F)c1N]
Fenvalerate
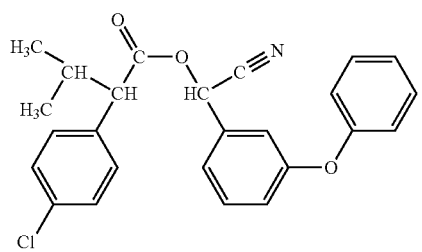 [SMILES: CC(C)C(C(=O)OC(C#N)c1cccc(Oc2ccccc2)c1)c1ccc(Cl)cc1]
Fluazifop-P-butyl
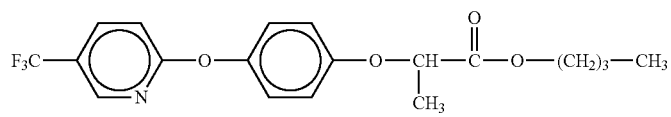
Flufenoxuron
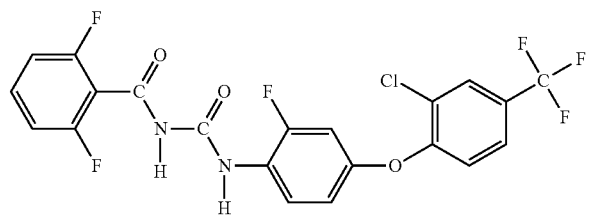 [SMILES: O=C(NC(=O)c1c(F)cccc1F)Nc1ccc(Oc2ccc(C(F)(F)F)cc2Cl)cc1F]
Hexazinone
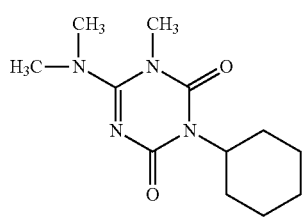 [SMILES: CN(C)c1nc(=O)n(C2CCCCC2)c(=O)n1C]

-continued
Lambda-cyhalothrin
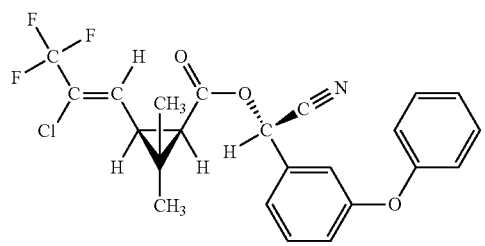
(S)-alcohol (Z)-(1R)-cis-acid
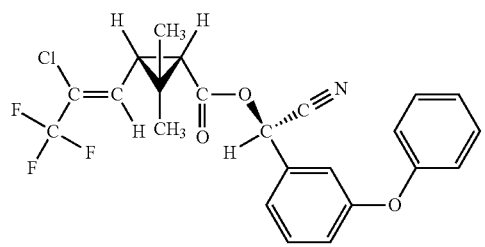
(R)-alcohol (Z)-(1S)-cis-acid
Methomyl
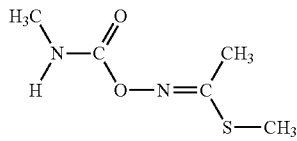
Permethrin
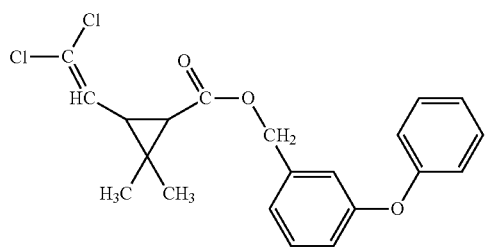 [SMILES: CC1(C)C(C=C(Cl)Cl)C1C(=O)OCc1cccc(Oc2ccccc2)c1]
Prochloraz
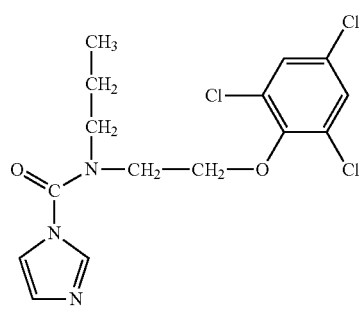 [SMILES: CCCN(CCOc1c(Cl)cc(Cl)cc1Cl)C(=O)n1ccnc1]
Propiconazole
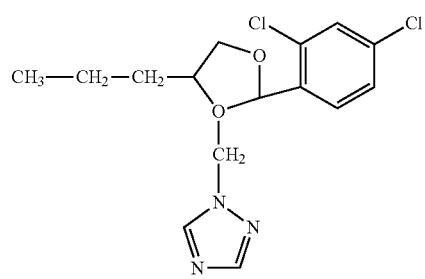

| Tebuconazole | 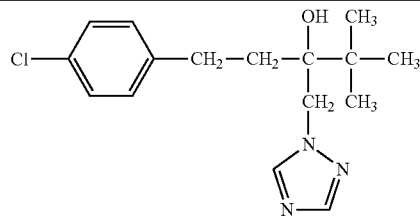 |
|---|---|

These products and names are known to a person skilled in the art. It is possible to combine several plant-protection active products.

Emulsifying Agent c)

The plant-protection formulation can comprise an emulsifying agent, typically and preferably a surfactant. The emulsifying agents are agents intended to facilitate the emulsification or the dispersion, after bringing the formulation into contact with water, and/or to stabilize (over time and/or with regard to the temperature) the emulsion or the dispersion, for example by preventing sedimentation.

The surfactants are known compounds which exhibit a molar mass which is generally relatively low, for example less than 1000 g/mol. The surfactant can be an anionic surfactant, in the salified or acid form, a nonionic surfactant, preferably a polyalkoxylated surfactant, a cationic surfactant or an amphoteric surfactant (term also including zwitterionic surfactants). A mixture or a combination of these surfactants may be involved.

Mention may be made, as examples of anionic surfactants, without the intention to be limited thereto, of:
  alkylsulfonic acids or arylsulfonic acids, optionally substituted by one or more hydrocarbon groups, the acid functional group of which is partially or completely salified, such as $C_8$-$C_{50}$, more particularly $C_8$-$C_{30}$ and preferably $C_{10}$-$C_{22}$ alkylsulfonic acids, benzenesulfonic acids or naphthalenesulfonic acids substituted by one to three $C_1$-$C_{30}$, preferably $C_4$-$C_{16}$, alkyl groups and/or $C_2$-$C_{30}$, preferably $C_4$-$C_{16}$, alkenyl groups.
  mono- or diesters of alkyl sulfosuccinic acids, the linear or branched alkyl part of which, optionally substituted by one or more hydroxyl and/or linear or branched $C_2$-$C_4$ alkoxyl (preferably ethoxyl, propoxyl or ethopropoxyl) groups.
  phosphate esters more particularly chosen from those comprising at least one saturated, unsaturated or aromatic and linear or branched hydrocarbon group comprising from 8 to 40, preferably from 10 to 30, carbon atoms, optionally substituted by at least one alkoxyl (ethoxyl, propoxyl or ethopropoxyl) group. In addition, they comprise at least one mono- or diesterified phosphate ester group, so that it is possible to have one or two free or partially or completely salified acid groups. The preferred phosphate esters are of the type of the mono- and diesters of phosphoric acid and of alkoxylated (ethoxylated and/or propoxylated) mono-, di- or tristyrylphenol or of alkoxylated (ethoxylated and/or propoxylated) mono-, di- or trialkylphenol, optionally substituted by one to four alkyl groups; of phosphoric acid and of an alkoxylated (ethoxylated or ethopropoxylated) $C_8$-$C_{30}$, preferably $C_{10}$-$C_{22}$, alcohol; or of phosphoric acid and of a nonalkoxylated $C_8$-$C_{22}$, preferably $C_{10}$-$C_{22}$, alcohol.
  sulfate esters obtained from saturated or aromatic alcohols optionally substituted by one or more alkoxyl (ethoxyl, propoxyl or ethopropoxyl) groups and for which the sulfate functional groups exist in the free acid form or partially or completely neutralized. Mention may be made, by way of example, of the sulfate esters more particularly obtained from saturated or unsaturated $C_8$-$C_{20}$ alcohols which can comprise from 1 to 8 alkoxyl (ethoxyl, propoxyl or ethopropoxyl) units; the sulfate esters obtained from polyalkoxylated phenol substituted by 1 to 3 saturated or unsaturated $C_2$-$C_{30}$ hydrocarbon groups and in which the number of alkoxyl units is between 2 and 40; or the sulfate esters obtained from polyalkoxylated mono-, di- or tristyrylphenol in which the number of alkoxyl units varies from 2 to 40.

The anionic surfactants can be in the acid form (they are potentially anionic) or in a partially or completely salified form, with a counterion. The counterion can be an alkali metal, such as sodium or potassium, an alkaline earth metal, such as calcium, or also an ammonium ion of formula $N(R)_4^+$ in which R, which are identical or different, represent a hydrogen atom or a $C_1$-$C_4$ alkyl radical optionally substituted by an oxygen atom.

Mention may be made, as examples of nonionic surfactants, without the intention to be limited thereto, of:
  polyalkoxylated (ethoxylated, propoxylated or ethopropoxylated) phenols substituted by at least one $C_4$-$C_{20}$, preferably $C_4$-$C_{12}$, alkyl radical or substituted by at least one alkylaryl radical, the alkyl part of which is a $C_1$-$C_6$ alkyl part. More particularly, the total number of alkoxyl units is between 2 and 100. Mention may be made, by way of example, of polyalkoxylated mono-, di- or tri (phenylethyl)phenols or polyalkoxylated nonylphenols. Mention may be made, among ethoxylated and/or propoxylated, sulfated and/or phosphated, di- or tristyrylphenols, of the ethoxylated di(1-phenylethyl) phenol comprising 10 oxyethylene units, the ethoxylated di(1-phenylethyl)phenol comprising 7 oxyethylene units, the ethoxylated and sulfated di(1-phenylethyl) phenol comprising 7 oxyethylene units, the ethoxylated tri(1-phenylethyl)phenol comprising 8 oxyethylene units, the ethoxylated tri(1-phenylethyl)phenol comprising 16 oxyethylene units, the ethoxylated and sulfated tri(1-phenylethyl)phenol comprising 16 oxyethylene units, the ethoxylated tri(1-phenylethyl)phenol comprising 20 oxyethylene units or the ethoxylated and phosphated tri(1-phenylethyl)phenol comprising 16 oxyethylene units.
  polyalkoxylated (ethoxylated, propoxylated or ethopropoxylated) $C_6$-$C_{22}$ fatty alcohols or acids. The number of the alkoxyl units is between 1 and 60. The term "ethoxylated fatty acid" includes both the products obtained by ethoxylation of a fatty acid with ethylene oxide and those obtained by esterification of a fatty acid with a polyethylene glycol.
  polyalkoxylated (ethoxylated, propoxylated or ethopropoxylated) triglycerides of vegetable or animal origin. The triglycerides resulting from lard, tallow, peanut oil, butter oil, cottonseed oil, linseed oil, olive oil, palm oil, grape seed oil, fish oil, soybean oil, castor oil, rapeseed oil, copra oil or coconut oil and comprising a total number of alkoxyl units of between 1 and 60 are thus suitable. The term "ethoxylated triglyceride" is targeted both at the products obtained by ethoxylation of a triglyceride with ethylene oxide and at those obtained by transesterification of a triglyceride with a polyethylene glycol.

optionally polyalkoxylated (ethoxylated, propoxylated or ethopropoxylated) sorbitan esters, more particularly cyclized sorbitol esters of $C_{10}$ to $C_{20}$ fatty acids, such as lauric acid, stearic acid or oleic acid, comprising a total number of alkoxyl units of between 2 and 50.

Emulsifiers of use are in particular the following products, all sold by Rhodia:

Soprophor® TSP/724: surfactant based on ethopropoxylated tristyrylphenol

Soprophor® 796/O: surfactant based on ethopropoxylated tristyrylphenol

Soprophor® CY 8: surfactant based on ethoxylated tristyrylphenol

Soprophor® BSU: surfactant based on ethoxylated tristyrylphenol

Alkamuls® RC: surfactant based on ethoxylated castor oil

Alkamuls® OR/36: surfactant based on ethoxylated castor oil

Alkamuls® T/20: surfactant based on a sorbitan ester

The formulation advantageously comprises at least 4%, preferably at least 5%, preferably at least 8%, by weight of dry matter, of at least one surfactant c).

It is mentioned that the solvent can be combined with an aromatic and/or nonaromatic surfactant.

Other Details with Regard to the Plant-Protection Formulation

The concentrated plant-protection formulation preferably does not comprise large amounts of water. Typically, the water content is less than 50% by weight, advantageously less than 25% by weight. It will generally be less than 10% by weight.

The formulation is preferably a liquid formulation, for example in the form of an emulsifiable concentrate (EC), a concentrated emulsion (EW) or a microemulsion (ME). In this case, it preferably comprises less than 500 g/l of water, more preferably less than 250 g/l. It will generally be less than 100 g/l.

The formulations can advantageously comprise:
a) from 4 to 60%, preferably from 10 to 50%, of the plant-protection product, by weight of active material,
b) from 10 to 92%, preferably from 20 to 80%, of the solvent, by weight,
c) from 4 to 60%, preferably from 5 to 50%, preferably from 8 to 25%, by weight of dry matter, of an emulsifier, preferably of a surfactant,
d) from 0 to 10% by weight of water.

The production of solid formulations, for example of formulations in which a liquid comprising the plant-protection product dissolved in the solvent is supported by a mineral and/or dispersed in a solid matrix, is not ruled out.

The formulation can, of course, comprise ingredients (or "additives") other than the plant-protection active product, the solvent(s), the optional emulsifying agent(s) and the optional water. It can in particular comprise viscosity-modifying agents, antifoaming agents, in particular silicone antifoaming agents, sticking agents, anti-leaching agents, inert fillers, in particular inorganic fillers, antifreeze agents, and the like.

The formulations can in particular comprise additives, referred to as "other additives", not included in the definition of the products a), b) or c), such as:

other solvents, generally in a small amount, that is to say in a smaller amount than the solvent of the solvent system which is present in the smallest amount. An other solvent is not understood as forming part of the solvent system. Mention is in particular made, as other solvents, of the solvents of the family of the phosphates, phosphonates or phosphine oxides, such as TEBP, TBP, TEPO or DBBP. Mention is also made of alkyldimethylamides where the alkyl is a $C_6$-$C_{18}$ alkyl, in particular those sold under the Genagen brand. Mention is also made of ester lactates, in particular those sold under the Purasolv brand. Mention is also made of methyl esters of fatty acids, in particular those sold under the Phytorobe brand. Mention is also made of diacid diesters ("DiBasic Esters"), in particular those sold by Rhodia under the Rhodiasolv RPDE and Rhodiasolv DIB brands. Mention is also made of hydrocarbon fractions, cyclic amides, such as NMP, and lactones. Mention is also made of the bis(dialkylamides) described in the document WO 2008/074837.

crystallization inhibitors. They can be the solvents mentioned above. They can also be nonpolyalkoxylated fatty acids or fatty alcohols. Mention is made, for example, of the product Alkamuls® OL700, sold by Rhodia.

Conventional processes for the preparation of plant-protection formulations or of mixtures of solvents can be employed. It is possible to carry out simple mixing of the constituents.

The concentrated plant-protection formulation is intended to be spread over a cultivated field or a field to be cultivated, for example of soya, generally after diluting in water, in order to obtain a dilute composition. Diluting is generally carried out by the farmer, directly in a tank (tank-mix), for example in the tank of a device intended to spread the composition. The addition by the farmer of other plant-protection products, for example fungicides, herbicides, pesticides or insecticides, or fertilizers is not ruled out. Thus, the formulation can be used to prepare a dilute composition in water of the plant-protection active product by mixing at least one part by weight of concentrated formulation with at least 10 parts by weight of water, preferably less than 1000 parts by weight of water. The degrees of dilution and the amounts to be applied to the field generally depend on the plant-protection product and on the dose desirable for treating the field; this can be determined by the farmer.

Other details or advantages may become apparent in the light of the examples which follow, without implied limitation.

EXAMPLES

Example 1

Preparation of $CH_3$—$CH_2$—$CH(O\text{-IsoAm})$—$(CH_2)$—$CONMe_2$

The synthetic route is as follows:

Mw: 81.12     Mw: 88.15

-continued

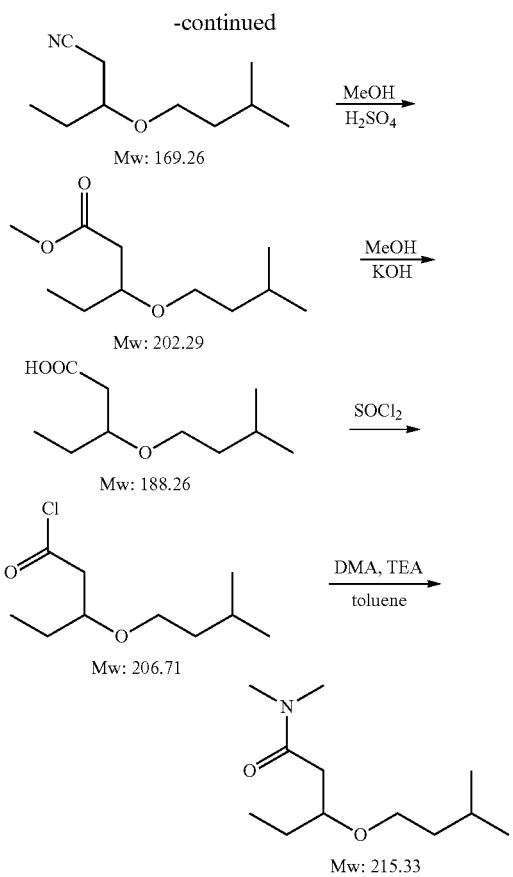

First Stage:

450 g (5.003 mol) of isoamyl alcohol, 10 g (0.06 mol) of Triton B (benzyltrimethylammonium hydroxide) and 414.1 g (5.003 mol) of 2PN (2-pentenenitrile) are charged at ambient temperature and kept stirred at 35±4° C. for 12 hours under a nitrogen blanket, 609.7 g of product of stage 1 (3-(isopentyloxy)pentanenitrile) are obtained with a yield of 72% and a purity of 98.8%.

Second Stage:

1507 ml (37.44 mol) of methanol, 350 ml (6.24 mol) of concentrated sulfuric acid with a density of 1.84 and 543 g (3.12 mol) of product of stage 1 are mixed and brought to reflux (80° C.) with stirring for 12 hours.

When the reaction is complete, the medium is poured onto 1500 ml of ice-cold water and then extracted with two times 300 ml of ethyl acetate. The combined organic phases are washed with an aqueous sodium hydrogencarbonate solution to pH 7-8. After evaporation of the ethyl acetate, 515 g of crude product of stage 2 (methyl 3-(isopentyloxy)pentanoate) are obtained i.e. a yield of 81.6%.

Third Stage:

623 g (3.08 mol) of crude product of stage 2, 1750 ml (43.5 mol) of methanol and 233 g (3.39 mol) of 85% potassium hydroxide and stirred at 55° C. for 12 hours.

When the reaction is complete, the methanol is evaporated and the medium is acidified to pH 4-5 with a dilute aqueous hydrochloric acid solution.

The medium is extracted with two times 500 ml of ethyl acetate. The organic phases are combined and the ethyl acetate is removed by evaporation, resulting in 520 g, i.e. 90% yield, of product of stage 3 (3-(isopentyloxy)pentanoic acid) with a purity of 98%.

Fourth Stage:

372 g (1.94 mol) of crude product of stage 3 and 465 g (3.89 mol) of thionyl chloride are stirred at 55° C. for 4 hours. When the reaction is complete, the thionyl chloride is evaporated, resulting in 380 g, i.e. a yield of 95.7%, of product of stage 4 (3-(isopentyloxy)pentanoyl chloride) having a purity of 95.5%.

Fifth Stage:

2500 ml of toluene, 450 ml (3.23 mol) of triethylamine, 280 ml (4.22 mol) of dimethylamine and 510 g (2.36 mol) of crude product of stage 4 are mixed at ambient temperature for 15 hours.

When the reaction is complete, the triethylammonium chloride formed is removed by filtration and washed with two times 300 ml of toluene. The toluene phases are combined and the toluene is removed by evaporation.

The product is subsequently washed with an aqueous sodium hydrogencarbonate solution to pH 7-8 and extracted with ethyl acetate.

The ethyl acetate is removed by evaporation and the product is purified by fractional distillation (boiling point: 105° C./100 Pa).

400 g of product of stage 5,3-isopentyloxy-N,N-dimethyl-pentanamide, are obtained, i.e. a yield of 79%, with a purity of 98.3%.

Example 2

Preparation of $CH_3$—$CH_2$—$CH(OMe)$-$(CH_2)$—$CONMe_2$

The preparation is carried out in a similar way to example 1, the isoamyl alcohol being replaced with methanol.

Example 3

Preparation of $CH_3$—$CH_2$—$CH(OCyclo)$-$(CH_2)$—$CONMe_2$

The synthetic route is as follows:

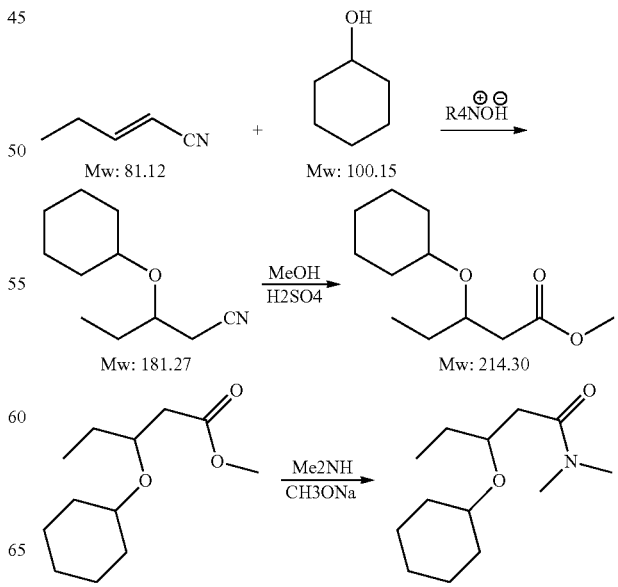

First Stage:

1100 ml (10.200 mol) of cyclohexanol and 28 g (0.067 mol) of Triton B (benzyltrimethylammonium hydroxide) are charged under a nitrogen blanket. 800 g (9.862 mol) of 2PN (2-pentenenitrile) are slowly charged while maintaining the temperature at 20±5° C. and then the mixture is maintained at ambient temperature for 38 hours while monitoring the reaction by gas chromatography. The conversion obtained is approximately 60% for the main compound. The catalyst is neutralized by the addition of acetic acid and then the intermediate is isolated by distillation under reduced pressure.

560 g of product of stage 1 (3-(cyclohexanoxy)pentanenitrile) are obtained with a purity of greater than 90%.

Second Stage:

1325 ml (33.10 mol) of methanol, 358 ml (6.62 mol) of concentrated sulfuric acid with a density of 1.84 and 600 g (3.31 mol) of product of stage 1 are mixed and brought to reflux (80° C.) with stirring for 12 hours.

When the reaction is complete, the medium is poured onto 1500 ml of ice-cold water and then extracted with two times 300 mol of ethyl acetate. The combined organic phases are washed with an aqueous sodium hydrogencarbonate solution to a pH 7-8. After evaporation of the ethyl acetate, 534 g of crude product of stage 2 (methyl 3-(cyclohexyloxy)pentanoate) are obtained. This intermediate is then distilled under reduced pressure to produce 497 g of product having a purity of greater than 90%, i.e. a yield of 70.2%.

Third Stage:

284.5 g of a 46% solution of N,N-dimethylamine in methanol (2.93 mol of DMA) are charged to a 1 l reactor. This solution is cooled to 0° C.±2° C.

The condenser of the reactor is supplied with aqueous glycol solution at 2° C.

The following are introduced onto the solution of N,N-dimethylamine in methanol:
  573 g of methyl 3-(cyclohexyloxy)pentanoate (2.68 mol) obtained at the conclusion of the second stage,
  22.9 g of solution of $CH_3ONa$ in methanol (strength of the solution 25% by weight).

The $CH_3ONa$ is introduced over 5 minutes with vigorous stirring.

The temperature of the reaction mass is brought to the temperature of 25° C. over 2 hours.

The progress of the reaction is monitored by GC analysis.

| | Degree of conversion % |
|---|---|
| Maintenance at 25° C. for 3 h | 31.67 |
| Maintenance at 25° C. for 27 h | 68.33 |
| Maintenance at 25° C. for 46 h | 72.75 |
| Maintenance at 25° C. for 118 h | 93.78 |

Additions of $CH_3ONa$ and of N,N-dimethylamine are carried out at the following times:

| Time (h) | Addition |
|---|---|
| 29 | 32.7 g of DMA in methanol (strength 37.5%) |
| 46 | 79.7 g of DMA (introduction at 0° C.) |
| 52 | 5 g of $CH_3ONa$ in methanol (strength of the solution 25% by weight) |

Isolation of the Product

The treatments described in detail below are carried out:
Removal of the DMA:
  The excess DMA and a portion of the methanol are distilled off under reduced pressure (P<30 mbar) at a temperature of less than 25° C.
  weight distilled 293 g.
Neutralization of the Catalyst:
  addition of 50 g of water and then of 356 g of aqueous hydrochloric acid solution (3.4%).
  The final pH of the aqueous phase is 7.01.
  The aqueous phase is separated by settling and the organic phase is washed with 300 g of water.
Drying of the Organic Phase:
  120 g of cyclohexane are added to the organic phase and the mixture is concentrated under partial vacuum (pressure<21 mbar/bulk temperature<50° C.).
  Reaction mass obtained: 533.8 g of a pale yellow solution.
Its composition is as follows:
  $CH_3$—$CH_2$—CH(OCyclo)-($CH_2$)—$CONMe_2$: 87.69%
  Methyl 3-(cyclohexyloxy)pentanoate: 7.43%
  Impurities: 4.88%
  The molar yield is 76%.
Purification
  987 g of the reaction mass obtained according to the above protocol are purified by topping.
Topping Conditions:
  pressure<2 mbar
  bulk temperature from 25 to 90° C.
  temperature of the distillates from 25 to 76° C.
  weight distilled 240 g
  Reaction mass obtained: 729 g of a pale yellow solution. It is 93% composed of $CH_3$—$CH_2$—CH(OCyclo)-($CH_2$) $CONMe_2$ Examples 4 to 7

Uses as Solvents—Plant-Protection Formulations

Formulations of various plant-protection active principles, of emulsifiable concentrate (EC) type, are prepared by mixing the ingredients.

The formulations comprise:
  the active principle, in an amount by weight (of active material) shown in the table below,
  10% by weight of surfactant Alkamuls® RC, sold by Rhodia,
  and, as solvent, the remainder of compound of the examples.

The examples 4 are comparative examples, where use is made, as solvent, of the product Rhodiasolv® ADMA 10, Rhodia (Asia Pacific region): Solvent alkyldimethylamide.

The following tests are carried out:
  Visual observation at 25° C.—The appearance of the formulation is recorded and possibly the presence of crystals is registered.
  Visual observation at 0° C.—The formulation is placed at 0° C. for 7 days and the appearance of the formulation is recorded and possibly the presence of crystals is registered (CIPAC test MT 39).
  Visual observation at 0° C. with nucleation: A crystal of the active material is introduced into the formulation which has spent 7 days at 0° C. for nucleation and the formulation is again placed at 0° C. for 7 days. The appearance of the formulation is recorded and possibly the presence of crystals is registered.

| Example | Solvent | Active principle | Appearance at 25° C. | Appearance at 0° C. | Appearance at 0° C. with nucleation |
|---|---|---|---|---|---|
| 4.1C | Rhodiasolv ® ADMA 10 | Alachlor-48% | Clear | Crystals | Crystals |
| 4.5C | Rhodiasolv ® ADMA 10 | Triadimenol 23% | Clear | Clear | Crystals |
| 4.6C | Rhodiasolv ® ADMA 10 | Trifluralin 40% | Clear | Clear | Crystals |
| 4.7C | Rhodiasolv ® ADMA 10 | Oxyfluorfen 22% | Clear | Clear | Crystals |
| 4.11C | Rhodiasolv ® ADMA 10 | Propoxur 20% | Clear | Clear | Crystals |
| 5.1 | Example 1 | Alachlor-48% | Clear | Clear | Crystals |
| 5.2 | Example 1 | Phenmedipham-16% | Clear | Clear | Clear |
| 5.3 | Example 1 | Propanil-36% | Clear | Clear | Clear |
| 5.4 | Example 1 | Tebuconazole-25% | Clear | Clear | Clear |
| 5.9 | Example 1 | Alpha-cypermethrin 10% | Clear | Clear | Clear |
| 6.1 | Example 2 | Alachlor-48% | Clear | Clear | Crystals |
| 6.3 | Example 2 | Propanil-36% | Clear | Clear | Clear |
| 6.4 | Example 2 | Tebuconazole-25% | Clear | Clear | Clear |
| 6.5 | Example 2 | Triadimenol 23% | Clear | Clear | Clear |
| 6.6 | Example 2 | Trifluralin 40% | Clear | Clear | Clear |
| 6.7 | Example 2 | Oxyfluorfen 22% | Clear | Clear | Clear |
| 6.8 | Example 2 | Chlorpyrifos 40% | Clear | Clear | Clear |
| 6.9 | Example 2 | Alpha-cypermethrin 10% | Clear | Clear | Clear |
| 6.11 | Example 2 | Propoxur 20% | Clear | Clear | Clear |
| 7.1 | Example 3 | Alachlor-48% | Clear | Clear | Clear |
| 7.2 | Example 3 | Phenmedipham 16% | Clear | Clear | Clear |
| 7.3 | Example 3 | Propanil-36% | Clear | Clear | Clear |
| 7.4 | Example 3 | Tebuconazole 25% | Clear | Clear | Clear |
| 7.5 | Example 3 | Triadimenol 23% | Clear | Clear | Clear |
| 7.6 | Example 3 | Trifluralin 40% | Clear | Clear | Clear |
| 7.7 | Example 3 | Oxyfluorfen 22% | Clear | Clear | Clear |
| 7.8 | Example 3 | Chlorpyrifos 40% | Clear | Clear | Clear |
| 7.9 | Example 3 | Alpha-cypermethrin 10% | Clear | Clear | Clear |
| 7.10 | Example 3 | Difenoconazole 25% | Clear | Clear | Clear |
| 7.11 | Example 3 | Propoxur 20% | Clear | Clear | Clear |

Example 8

Formulation of Tebuconazole

The following EC formulation is prepared:

| | |
|---|---|
| Tech. tebuconazole, 97% | 258 g/l |
| Solvent of example 3 | 608 g/l |
| Geronol ® TBE-724 (surfactant, Rhodia) | 150 g/l |

The properties of the formulation are evaluated after the preparation:
Density at 20° C.: 1.016
pH (5% solution): 6.3

Emulsification (CIPAC test, at a concentration of 1% at 30° C., after 24 hours

| A | D | C |
|---|---|---|
| 0t | O | O |

Emulsification (CIPAC test, at a concentration of 5% at 30° C., after 2 hours

| A | D | C |
|---|---|---|
| 0t | O | O |

Appearance at 0° C.: Hazy solution, becoming clear at ambient temperature

Appearance at 54° C.: Clear solution

The properties of the formulation are evaluated after 14 days at 54° C.:

pH (5% solution): 5.1

Emulsification (CIPAC test, at a concentration of 1% at 30° C., after 4 hours

| A | D | C |
|---|---|---|
| 0t | O | O |

Emulsification (CIPAC test, at a concentration of 5% at 30° C., after 4 hours

| A | D | C |
|---|---|---|
| 0t | O | O |

Appearance at 0° C.: Hazy solution, becoming clear at ambient temperature

Appearance at 54° C.: Clear solution

What is claimed is:

1. An ether-amide compound having formula (I):

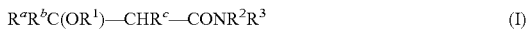

$R^aR^bC(OR^1)$—$CHR^c$—$CONR^2R^3$     (I)

wherein:
- $R^a$, $R^b$, and $R^c$ are each a hydrogen atom, or a linear, or branched alkyl radical, wherein at least one of $R^a$, $R^b$, and $R^c$ is other than a hydrogen atom,
- $R^1$ is an $R^{r1}$ or $-(AO)_nR^{r1}$ group, wherein:
  - $R^{r1}$ is a hydrocarbon radical having an average number of carbon atoms ranging from 1 to 36 which are saturated or unsaturated, linear, or branched, optionally cyclic and optionally aromatic, with the proviso that said aromatic radicals may contain a heteroatom in an aromatic ring,
  - the radicals AO, which may be identical or different, are each a radical of formula —$CH_2$—$CH_2$—O—, —CHMe—$CH_2$—O—, or —$CH_2$—CHMe—O—,
  - n is an average number greater than or equal to 0,
- $R^2$ and $R^3$, which may be identical or different, are each a hydrocarbon radical having an average number of carbon atoms ranging from 1 to 36 which are saturated or unsaturated, linear, or branched, optionally cyclic, optionally aromatic and optionally substituted, with the proviso that $R^2$ and $R^3$ may together optionally form a ring member including the nitrogen atom to which they are bonded, which ring member is optionally substituted and/or optionally includes an additional heteroatom, said ether-amide compound having a melting point of less than or equal to 20° C.

2. An ether-amide compound, having one of the following formulae:

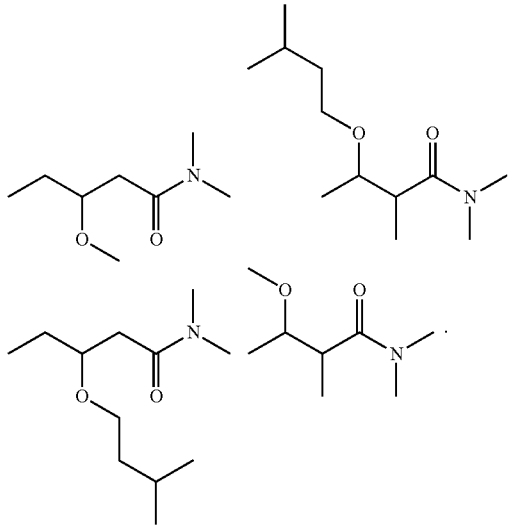

3. A solvent or cosolvent, comprising an ether-amide compound having formula (I):

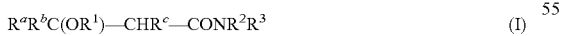

$R^aR^bC(OR^1)$—$CHR^c$—$CONR^2R^3$     (I)

wherein:
- $R^a$, $R^b$, and $R^c$ are each a hydrogen atom, or a linear, or branched alkyl radical, wherein at least one of $R^a$, $R^b$, and $R^c$ is other than a hydrogen atom,
- $R^1$ is an $R^{r1}$ or $-(AO)_nR^{r1}$ group, wherein:
  - $R^{r1}$ is a hydrocarbon radical having an average number of carbon atoms ranging from 1 to 36 which are saturated or unsaturated, linear, or branched, optionally cyclic and optionally aromatic, with the proviso that said aromatic radicals may contain a heteroatom in an aromatic ring,
  - the radicals AO, which may be identical or different, are each a radical of formula —$CH_2$—$CH_2$—O—, —CHMe—$CH_2$—O—, or —$CH_2$—CHMe—O—,
  - n is an average number greater than or equal to 0,
- $R^2$ and $R^3$, which may be identical or different, are each a hydrocarbon radical having an average number of carbon atoms ranging from 1 to 36 which are saturated or unsaturated, linear, or branched, optionally cyclic, optionally aromatic and optionally substituted, with the proviso that $R^2$ and $R^3$ may together optionally form a ring member including the nitrogen atom to which they are bonded, which ring member is optionally substituted and/or optionally includes an additional heteroatom.

4. A plant-protection formulation, a cleaning formulation, a stripping formulation, a degreasing formulation, a lubricating formulation, a coating formulation, a pigment or ink formulation, or a plastic formulation, comprising an ether-amide compound having formula (I):

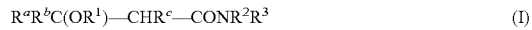

$R^aR^bC(OR^1)$—$CHR^c$—$CONR^2R^3$     (I)

wherein:
- $R^a$, $R^b$, and $R^c$ are each a hydrogen atom, or a linear, or branched alkyl radical, wherein at least one of $R^a$, $R^b$, and $R^c$ is other than a hydrogen atom,
- $R^1$ is an $R^{r1}$ or $-(AO)_nR^{r1}$ group, wherein:
  - $R^{r1}$ is a hydrocarbon radical having an average number of carbon atoms ranging from 1 to 36 which are saturated or unsaturated, linear, or branched, optionally cyclic and optionally aromatic, with the proviso that said aromatic radicals may contain a heteroatom in an aromatic ring,
  - the radicals AO, which may be identical or different, are each a radical of formula —$CH_2$—$CH_2$—O—, —CHMe—$CH_2$—O—, or —$CH_2$—CHMe—O—,
  - n is an average number greater than or equal to 0,
- $R^2$ and $R^3$, which may be identical or different, are each a hydrocarbon radical having an average number of carbon atoms ranging from 1 to 36 which are saturated or unsaturated, linear, or branched, optionally cyclic, optionally aromatic and optionally substituted, with the proviso that $R^2$ and $R^3$ may together optionally form a ring member including the nitrogen atom to which they are bonded, which ring member is optionally substituted and/or optionally includes an additional heteroatom.

5. A plant-protection formulation comprising a plant-protection active product and an ether-amide compound having formula (I):

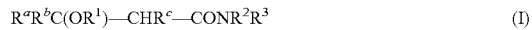

$R^aR^bC(OR^1)$—$CHR^c$—$CONR^2R^3$     (I)

wherein:
- $R^a$, $R^b$, and $R^c$ are each a hydrogen atom, or a linear, or branched alkyl radical, wherein at least one of $R^a$, $R^b$, and $R^c$ is other than a hydrogen atom,
- $R^1$ is an $R^{r1}$ or $-(AO)_nR^{r1}$ group, wherein:
  - $R^{r1}$ is a hydrocarbon radical having an average number of carbon atoms ranging from 1 to 36 which are saturated or unsaturated, linear, or branched, optionally cyclic and optionally aromatic, with the proviso that said aromatic radicals may contain a heteroatom in an aromatic ring,
  - the radicals AO, which may be identical or different, are each a radical of formula —$CH_2$—$CH_2$—O—, —CHMe—$CH_2$—O—, or —$CH_2$—CHMe—O—,
  - n is an average number greater than or equal to 0,
- $R^2$ and $R^3$, which may be identical or different, are each a hydrocarbon radical having an average number of carbon atoms ranging from 1 to 36 which are saturated or unsaturated, linear, or branched, optionally cyclic, optionally aromatic and optionally substituted, with the proviso that $R^2$ and $R^3$ may together optionally form a ring member including the nitrogen atom to which they are bonded, which ring member is optionally substituted and/or optionally includes an additional heteroatom.

6. The plant-protection formulation as defined by claim 5, wherein the plant-protection active product is selected from the group consisting of a herbicide, an insecticide, an acaricide, a fungicide, and a rodenticide.

7. The solvent or cosolvent of claim 3, wherein the total number of carbon atoms of the ether-amide, excluding the $R^1$, $R^2$, and $R^3$ radicals, is 4, 5, or 6.

8. The solvent or cosolvent of claim 3, wherein the ether-amide compound is of formula (I), wherein:
   $R^c$ =H and $R^b$ =H, or
   $R^c$=Me and $R^b$ =H, or
   $R^c$=H and $R^b$=Me.

9. The solvent or cosolvent of claim 3, wherein the ether-amide compound is of formula (I) wherein $R^a$ is a methyl or ethyl radical.

10. The solvent or cosolvent of claim 3, wherein the ether-amide compound is of formula (I), wherein:
    $R^c$ =H and $R^b$ =H and $R^a$=Et, or
    $R^c$=Me and $R^b$=H and $R^a$=Me, or
    $R^c$=H and $R^b$=Me and $R^a$=Me.

11. The solvent or cosolvent of claim 3, wherein the ether-amide compound is of formula (I) wherein $R^2$ and $R^3$, which may be identical or different, are each selected from the group consisting of methyl, ethyl, propyl (n-propyl), isopropyl, n-butyl, isobutyl, n-pentyl, amyl, isoamyl, hexyl, and cyclohexyl radicals, or may together form, with the nitrogen atom from which they depend, a morpholine, piperazine, or piperidine heterocycle.

12. The solvent or cosolvent of claim 3, wherein the ether-amide compound is of formula (I), wherein $R^2$ and $R^3$ are each a methyl radical.

13. The solvent or cosolvent of claim 3, wherein the ether-amide compound is of formula (I), wherein $R^{'1}$ is selected from the group consisting of methyl, ethyl, propyl, isopropyl, n-butyl, isobutyl, n-pentyl, isopentyl, isoamyl, n-hexyl, cyclohexyl, n-octyl, isooctyl, 2-ethylhexyl, tridecyl, phenyl, and benzyl radicals.

14. The plant-protection formulation, cleaning formulation, stripping formulation, degreasing formulation, lubricating formulation, coating formulation, pigment or ink formulation, or plastic formulation of claim 4, wherein the total number of carbon atoms of the ether-amide, excluding the $R^1$, $R^2$, and $R^3$ radicals, is 4, 5, or 6.

15. The plant-protection formulation, cleaning formulation, stripping formulation, degreasing formulation, lubricating formulation, coating formulation, pigment or ink formulation, or plastic formulation of claim 4, wherein the ether-amide compound is of formula (I), wherein:
    $R^c$ =H and $R^b$=H, or
    $R^c$=Me and $R^b$=H, or
    $R^c$=H and $R^b$=Me.

16. The plant-protection formulation, cleaning formulation, stripping formulation, degreasing formulation, lubricating formulation, coating formulation, pigment or ink formulation, or plastic formulation of claim 4, wherein the ether-amide compound is of formula (I), wherein $R^a$ is a methyl or ethyl radical.

17. The plant-protection formulation, cleaning formulation, stripping formulation, degreasing formulation, lubricating formulation, coating formulation, pigment or ink formulation, or plastic formulation of claim 4, wherein the ether-amide compound is of formula (I), wherein:
    $R^c$=H and $R^b$ =H and $R^a$=Et, or
    $R^c$=Me and $R^b$=H and $R^a$=Me, or
    $R^c$=H and $R^b$=Me and $R^a$=Me.

18. The plant-protection formulation, cleaning formulation, stripping formulation, degreasing formulation, lubricating formulation, coating formulation, pigment or ink formulation, or plastic formulation of claim 4, wherein the ether-amide compound is of formula (I), wherein $R^2$ and $R^3$, which may be identical or different, are each selected from the group consisting of methyl, ethyl, propyl (n-propyl), isopropyl, n-butyl, isobutyl, n-pentyl, amyl, isoamyl, hexyl, and cyclohexyl radicals, or may together form, with the nitrogen atom from which they depend, a morpholine, piperazine, or piperidine heterocycle.

19. The plant-protection formulation, cleaning formulation, stripping formulation, degreasing formulation, lubricating formulation, coating formulation, pigment or ink formulation, or plastic formulation of claim 4, wherein the ether-amide compound is of formula (I), wherein $R^2$ and $R^3$ are each a methyl radical.

20. The plant-protection formulation, cleaning formulation, stripping formulation, degreasing formulation, lubricating formulation, coating formulation, pigment or ink formulation, or plastic formulation of claim 4, wherein the ether-amide compound is of formula (I) wherein $R^{'1}$ is selected from the group consisting of methyl, ethyl, propyl, isopropyl, n-butyl, isobutyl, n-pentyl, isopentyl, isoamyl, n-hexyl, cyclohexyl, n-octyl, isooctyl, 2-ethylhexyl, tridecyl, phenyl, and benzyl radicals.

21. The plant-protection formulation of claim 5, wherein the total number of carbon atoms of the ether-amide, excluding the $R^1$, $R^2$, and $R^3$ radicals, is 4, 5, or 6.

22. The plant-protection formulation of claim 5, wherein the ether-amide compound is of formula (I), wherein:
    $R^c$ =H and $R^b$ =H, or
    $R^c$=Me and $R^b$=H, or
    $R^c$=H and $R^b$=Me.

23. The plant-protection formulation of claim 5, wherein the ether-amide compound is of formula (I) wherein $R^a$ is a methyl or ethyl radical.

24. The plant-protection formulation of claim 5, wherein the ether-amide compound is of formula (I), wherein:
    $R^c$=H and $R^b$=H and $R^a$=Et, or
    $R^c$=Me and $R^b$=H and $R^a$=Me, or
    $R^c$=H and $R^b$=Me and $R^a$=Me.

25. The plant-protection formulation of claim 5, wherein the ether-amide compound is of formula (I), wherein $R^2$ and $R^3$, which may be identical or different, are each selected from the group consisting of methyl, ethyl, propyl (n-propyl), isopropyl, n-butyl, isobutyl, n-pentyl, amyl, isoamyl, hexyl, and cyclohexyl radicals, or may together form, with the nitrogen atom from which they depend, a morpholine, piperazine, or piperidine heterocycle.

26. The plant-protection formulation of claim 5, wherein the ether-amide compound is of formula (I), wherein $R^2$ and $R^3$ are each a methyl radical.

27. The plant-protection formulation of claim 5, wherein the ether-amide compound is of formula (I), wherein $R^{'1}$ is selected from the group consisting of methyl, ethyl, propyl, isopropyl, n-butyl, isobutyl, n-pentyl, isopentyl, isoamyl, n-hexyl, cyclohexyl, n-octyl, isooctyl, 2-ethylhexyl, tridecyl, phenyl, and benzyl radicals.

* * * * *